United States Patent [19]

Shinohara et al.

[11] Patent Number: 4,678,755

[45] Date of Patent: Jul. 7, 1987

[54] AUTOMATIC CHEMICAL ANALYZER

[75] Inventors: Hiroo Shinohara, Ootawara; Toshiaki Imai, Tochigi, both of Japan

[73] Assignee: Kabushiki Kaisha Toshiba, Kawasaki, Japan

[21] Appl. No.: 760,148

[22] Filed: Jul. 29, 1985

[30] Foreign Application Priority Data

Jul. 30, 1984 [JP] Japan ................. 59-161377

[51] Int. Cl.$^4$ ............................. G01N 35/00
[52] U.S. Cl. ...................... 436/43; 422/67; 436/47
[58] Field of Search ............ 422/67, 64; 436/47, 436/50, 43; 364/497, 499

[56] References Cited

U.S. PATENT DOCUMENTS

| | | | |
|---|---|---|---|
| 3,960,497 | 6/1976 | Acord | 436/50 |
| 4,043,756 | 8/1977 | Sommervold | 422/67 |
| 4,158,545 | 6/1979 | Yamashita et al. | 436/47 |
| 4,276,051 | 6/1981 | Ginsberg et al. | 422/67 |
| 4,309,112 | 1/1982 | Ashley et al. | 422/68 |
| 4,539,296 | 9/1985 | Manabe | 422/67 |
| 4,566,110 | 1/1986 | Kolber | 422/91 |

FOREIGN PATENT DOCUMENTS 58-63854  4/1983  Japan ................. 436/50

*Primary Examiner*—Michael S. Marcus
*Attorney, Agent, or Firm*—Finnegan, Henderson, Farabow, Garrett & Dunner

[57] ABSTRACT

An automatic chemical analyzer performs calibration by comparing a measured value obtained by measuring a reaction solution, obtained by reacting a sample with a reagent, with a calibration curve corresponding to the analysis item. In the apparatus, a desired number of analysis items and calibration intervals corresponding to the analysis items are set by an input device, and stored in the memory. A control device has a counting device, and checks if the calibration interval stored in the memory has elapsed for each analysis item so as to supply calibration alarm data and/or calibration indication data in accordance with the checking result and upon interlocking with the counting device. A display displays at least one of the above data.

8 Claims, 10 Drawing Figures

| ANALYSIS ITEM | Na, K Cl | GLU | CO2 | GOT | CPK | CRTN |
|---|---|---|---|---|---|---|
| LAST CALIBRATION TIME | 0H | 0H | 0H | 0H | 0H | 0H |
| CALIBRATION INTERVAL | 3H | 2H | 1H | 4H | 4H | 24H |

FIG. 3
```
    15 JUN 84 01:06 READY
    CALIBRATION  MENU 1
NO.              NO.              NO.
 1 CO2  .        10      0        19 NA    0
 2 GLU   0       11      0        20 K     0
 3 GOT   0       12      0        21 CL    0
 4 CPT   0       13      0
 5 CRTN  0       14      0
 6       0       15      0
 7       0       16      0
 8       0       17      0
 9       0       18      0
```
6  3
FIG. 4
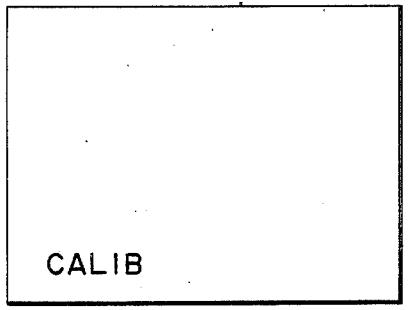
CALIB
FIG. 5
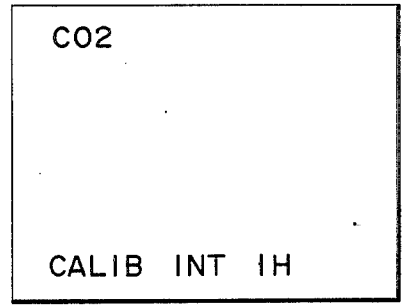
CO2
CALIB  INT  1H

FIG. 6

| ANALYSIS ITEM | Na,K,Cl | GLU | CO₂ | GOT | CPK | CRTN |
|---|---|---|---|---|---|---|
| AMOUNT OF REAGENT (mℓ) | 2.4 | 1.8 | | 0.9 | 0.9 | 2.4 |
| CALIBRATION INTERVAL | 3H | 2H | 1H | 4H | 4H | 24H |
| CALIBRATION TIME | | | | | | |
| 0 H | * | * | * | * | * | * |
| | | | * | | | |
| 2 | | * | * | | | |
| | * | | * | | | |
| 4 | | * | * | * | * | |
| | | | * | | | |
| 6 | * | * | * | | | |
| | | | * | | | |
| 8 | | * | * | * | * | |
| | * | | * | | | |
| 10 | | * | * | | | |
| | | | * | | | |
| 12 | * | * | * | * | * | |
| | | | * | | | |
| 14 | | * | * | | | |
| | * | | * | | | |
| 16 | | * | * | | | |
| | | | * | | | |
| 18 | * | * | * | * | * | |
| | | | * | | | |
| 20 | | * | * | | | |
| | * | | * | | | |
| 22 | | * | * | | | |
| | | | * | | | |
| 24 | * | * | * | * | * | * |

TIME DATA INITIALIZE ROUTINE

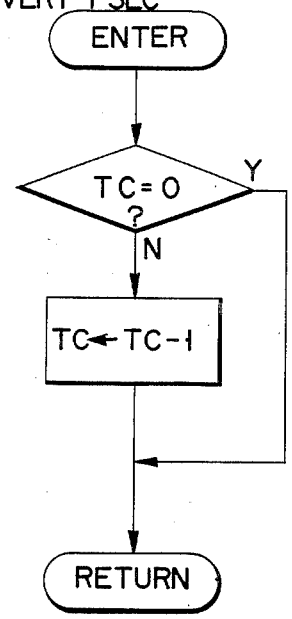
F I G. 9
INTERRUPT ROUTINE EVERY 1 SEC
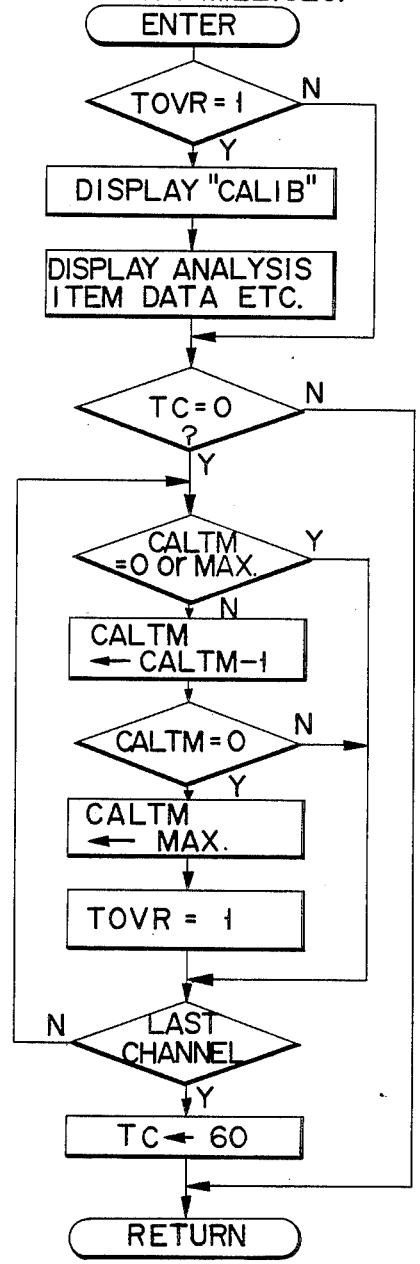
F I G. 10
INTERRUPT ROUTINE EVERY 100 MILLISEC.

AUTOMATIC CHEMICAL ANALYZER

BACKGROUND OF THE INVENTION

The present invention relates to an automatic chemical analyzer.

In an automatic chemical analyzer used in clinical examinations and the like, analysis is automatically performed as follows. Serum (i.e., a sample) taken from a patient as an analysis object is mixed, for reaction with a reagent corresponding to a desired analysis item. (The reagent is diluted, if necessary, before and/or after the sample is mixed with the reagent.) Light transmission through the reaction solution is measured so as to obtain an absorbancy. Alternatively, a potential difference between electrodes appropriately arranged in the reaction solution may be measured. The absorbancy or the electrode potential is compared with a calibration curve obtained, in advance, from the corresponding reagent and a standard substance, e.g., a standard serum, to thereby obtain a concentration of a specific component of the sample corresponding to either the absorbancy or the electrode potential.

In general, even if a reagent is kept at a low temperature of about 2° to 8° C., which is considered a preferable condition, reagent deterioration is evident. That is, since the reagent contains a plurality of drugs, characteristics of the reagent are degraded due to, e.g., reaction between the mixed drugs, resulting in poor measurement precision. For this reason, formation of a calibration curve using the standard serum (i.e., calibration) must be repeated at predetermined intervals.

However, in the automatic chemical analyzer, a number of analysis items are present, and reagents used in examinations for respective items exhibit various degradation speeds. For this reason, an interval (i.e., a "calibration interval") from an immediately preceding calibration curve to the next calibration is varied in accordance with the types of reagent, i.e., measurement items. In the conventional automatic chemical analyzer, calibration for each analysis item is not of particular concern. For example, when two analysis items having respective calibration intervals of 3 hours and 1 hour are present, calibration is performed at intervals of 1 hour even for the analysis item having the calibration interval of 3 hours. In this manner, when calibration is performed too frequently, much expensive standard serum and sample material are wasted, resulting in high cost. Similarly, a sample line conveying a reaction chamber for effective processing must be stopped for every calibration, thus wasting time.

In the conventional automatic chemical analyzer, since a calibration timing depends upon the judgment of an experienced clinician, an error in measurement precision can easily occur due to the difference in calibration timing of each clinician who must perform a predetermined operation at constant intervals for accurate calibration.

In order to calibrate an analysis item having a relatively short calibration interval, processing can be performed wherein an analysis item having a relatively long calibration interval is not calibrated. However, in order to realize such processing, the calibration interval for each analysis item must be stored, and calibration and other controls must be performed for each item, thus complicating the processing sequence and apparatus arrangement. For this reason, it is difficult to realize such processing in practice.

SUMMARY OF THE INVENTION

It is an object of the present invention to provide an automatic chemical analyzer which can reduce the frequency or the total number of times calibration must occur, i.e., reformation of a calibration curve, without complicating the arrangement of the apparatus, and so that a desired analysis precision can be achieved and maintained, thus reducing cost and time while improving the quality of the analysis.

According to the present invention, there is provided an automatic chemical analyzer in which a sample, as an analysis object, is mixed with a reagent so as to react therewith, and wherein the sample is analyzed in accordance with either an absorbancy, or an electrode potential obtained by measuring a reaction solution, and a calibration curve (obtained by using a standard substance in advance) corresponding to an analysis item, said automatic chemical analyzer comprising a device for setting a plurality of analysis items, calibration times and calibration intervals of calibration curves corresponding to the analysis items; a storage device for storing data set by the setting device; a control device operated by using the data stored in the storage device, the control device having a counting device and a device, interlocked with the counting device, for discriminating the calibration interval for each analysis item so as to generate calibration alarm data and calibration indication data corresponding to the analysis item to be calibrated; and a device for displaying the data generated from the control device.

According to the present invention, calibration alarm data and calibration indication data are displayed for each analysis item, while items whose calibration intervals have passed, as well as items for which calibration has been completed are displayed in a table. For this reason, there is provided an automatic chemical analyzer in which the frequency and number of times of the reformation of a calibration curve can be decreased to a minimum, excessive cost and time loss being thereby reduced.

BRIEF DESCRIPTION OF THE DRAWINGS

FIG. 3 is a view showing an example of a calibration menu displayed on a display device of the embodiment;

FIG. 4 shows calibration alarm data displayed by the display device;

FIG. 5 shows calibration indication data displayed by the display device;

FIG. 6 is a table showing the relationship between an analysis item, an amount of reagent, a calibration interval and a calibration time; and FIGS. 7 to 10 are flow charts showing a main part of processing in a control device of the embodiment.

DETAILED DESCRIPTION OF THE PREFERRED EMBODIMENT

Figures 1, 2:
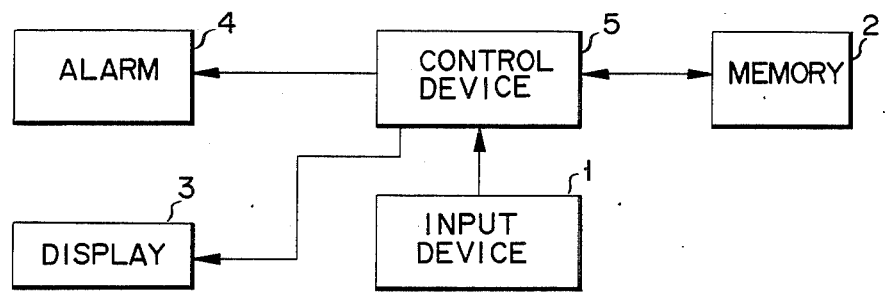
FIG. 1 is a block diagram showing an arrangement of an apparatus according to an embodiment of the present invention.
FIG. 2 is a table showing an example of a storage content stored in a storage device of the embodiment.

FIG. 1 shows a schematic arrangement of an automatic chemical analyzer according to an embodiment of the present invention.

The automatic chemical analyzer has an input device 1, a memory 2, a display 3, an alarm 4 and a control device 5 having a count function.

The input device 1 comprises, e.g., a keyboard, and supplies to the control device 5, in response to an input operation of an operator, input signals corresponding to analysis item data, calibration time data of the first calibration, calibration interval data and calibration-requesting data.

The memory 2 is controlled by the control device 5, and stores data associated with the last (immediately preceding) calibration time and the calibration interval for each analysis item. In accordance with the input operation from the input device 1, the data associated with the last calibration time and the calibration interval for each analysis item are transferred from the control device 5 to the memory 2, and stored therein.

The display 3 displays various data under the control of the control device 5. For example, in one case, a calibration menu 6 is displayed on the display 3, as shown in FIG. 3. In another case, the display 3 displays calibration alarm data (displayed as "CALIB") as shown in FIG. 4, as well as both calibration indication data, including analysis item data (e.g., displayed as "$CO_2$"), and the calibration interval data (e.g., displayed as "CALIB INT 1H") for each item, as shown in FIG. 5.

The operation of an automatic chemical analyzer having the above arrangement will be described with reference to a table of FIG. 6 showing the relation among the analysis items, the calibration intervals and the like, and flow charts of FIGS. 7-10 showing main processing in the control device 5.

Referring to FIG. 6, reference symbol GLU indicates glucose; GOT, transaminase; CPK, creatine phosphokinase; and CRTN, creatinine. Asterisks "*" indicate calibration times corresponding to calibration intervals for the respective analysis items.

An operator, e.g., a clinician operates the input device 1 so as to input, respective analysis item data Na, K, Cl, GLU, $CO_2$, GOT, CPK and CRTN, and the calibration times and calibration intervals (3 hours, 2 hours, 1 hour, 4 hours, 4 hours and 24 hours) corresponding to the analysis items and referred to as the CALINT data for each item. These data are stored in the memory 2 through the control device 5. When the operator depresses a start button for initiating the system, a measurement processing routine is executed.

Figure 7:
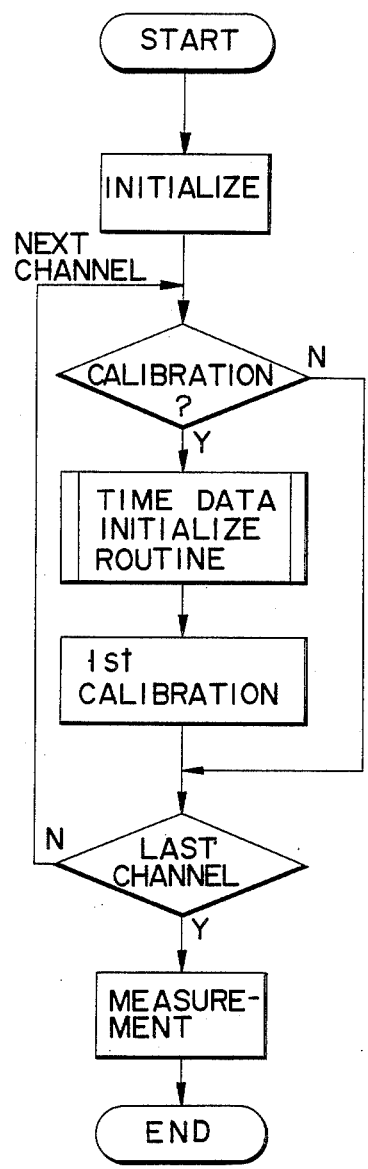
Figure 8:
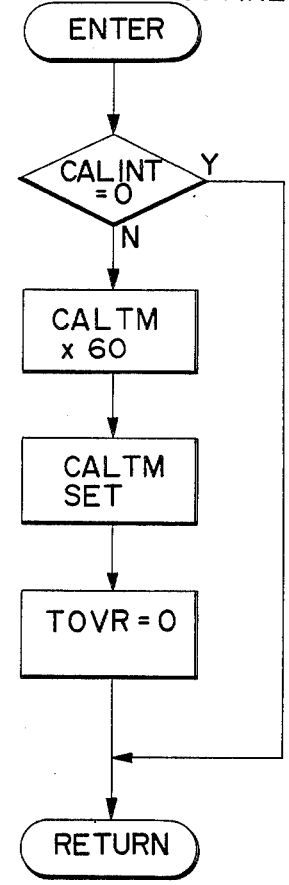

In the measurement processing routine, as shown in the flow chart of FIG. 7, initialization of the system is performed, and it is then checked if calibration is needed for each item. If no calibration is needed, discrimination of a last channel is performed, i.e., it is determined if processing for all channels is completed. Conversely, if calibration is needed, a time data initialization routine is executed as shown in the flow chart of FIG. 8, and the first calibration for the corresponding channel is performed. After the first calibration, the discrimination of the last channel, as described above, is performed. In the time data initialization routine of FIG. 8, it is checked if the data CALINT, indicating the calibration interval, is set. If the data CALINT is not set, i.e., if CALINT=0, the flow returns to the measurement processing routine and again goes to the first calibration processing. If CALINT≠0, since the data CALINT is set, the data CALINT, which is set in units of hours, is multiplied by 60 so as to be converted to units of minutes. The converted value is stored as time count data CALTM, and, thereafter, a time-over flag TOVR is cleared to 0. Then, the flow returns to the measurement processing routine, and goes to the first calibration processing.

If, by discrimination, it is detected that the current channel is not the last channel after the first calibration processing, i.e., a non-processed channel still remains, the flow returns to the step of determined if calibration is needed, and the same processing as described above is performed for the next item. If, by discrimination, it is detected that the current channel is the last channel of the last channel, i.e., the processing for all the channels is completed, the flow goes to measurement processing of the items for the sample.

In the measurement processing, reaction and photometry processes are performed in reaction and photometric units (neither are shown) in the analyzer.

Simultaneous therewith, the counting function of the control device 5 is started. For example, when 1 hour has passed, a signal indicating a calibration alarm is supplied from the control device 5 to the display 3 in accordance with the counting function, thereby displaying the calibration alarm data "CALIB". Then, the control device 5 causes the display 3 to display the calibration indication data. That is, after the calibration alarm data "CALIB", the analysis item "$CO_2$" and the calibration interval data (1 hour) "CALIB INT 1H" are simultaneously displayed as the calibration indication data on the display 3.

Such counting and alarm display operations in the control device 5 can be realized by means of two interrupt routines shown in FIGS. 9 and 10.

The interrupt processing shown in FIG. 9 is executed each second by a hardware timer (not shown). It is first checked if time counter data TC is 0. If TC=0, the flow returns to the measurement processing routine shown in FIG. 7, whereas, if TC≠0, the data TC is decremented by one.

The interrupt processing shown in FIG. 10 is executed for each msec by another hardware timer (not shown). When this interrupt processing is executed, it is checked if the time-over flag TOVR is 1. If TOVR=1, the calibration alarm data, i.e., "CALIB", and the calibration indication data (the analysis item and calibration interval data) are subsequently displayed on the display 3. Thereafter, it is checked if the time counter data TC is 0. Conversely, if TOVR≠1, it is immediately checked if TC=0.

If the time counter data TC=0, it is checked if the time count data CALTM is 0 or its maximum value (CALTM is not set at the maximum value as a setting time, but, rather, is set to be the maximum value only when time-over occurs, as will be described later). If Y (YES) in this step, the flow jumps to the step of checking if the current channel is the last channel. If the data CALTM is neither 0 nor the maximum value, the data CALTM is decremented by one. As a result, if the data CALTM is not 0, the flow jumps to the step of checking if the current channel is the last channel. However, if the data CALTM becomes 0 by decrement because the calibration interval has elapsed for the corresponding item, i.e., time-over occurs, the data CALTM is set at the maximum value, and the time-over flag is set at 1. Thereafter, the flow advances to the step of discriminating the last channel. In this manner, when the above processing for all the channels is completed, the data TC is set at 60, thus ending the interrupt processing and allowing the flow to return to the main routine. In the step of determining if TC=0, described above, if TC≠0, the interrupt processing also ends.

The operator recognizes these displayed data on the display 3, and requests the calibration curve calibration associated with the analysis item $CO_2$ by operating the input device 1.

Thus, calibration of only the analysis item $CO_2$ is performed. Simultaneously, the control device 5 updates the calibration time (an elapsed time from the beginning of measurement) associated with the analysis item $CO_2$ stored in the memory 2 from 0 (initial value) to 1 hour.

When 2 hours have elapsed from the above calibration time, the calibration alarm data "CALIB" is displayed on the display 3 by the counting function of the device 5, and the calibration indication data for the analysis items GLU and $CO_2$ are displayed by the device 5. That is, data and the calibration interval data ('hours and 1 hour) for the two analysis items are simultaneously or sequentially displayed on the display 3. The operator requests the calibration of the calibration curves corresponding to the analysis items GLU and $CO_2$ in accordance with this display. Then, the control device 5 updates to 2 hours the calibration times stored in the memory 2 and corresponding to the analysis items GLU and $CO_2$.

It should be noted that when the signal for displaying the calibration alarm data is supplied from the control device 5 to the display 3, it is simultaneously supplied to the alarm device 4, to produce an alarm sound.

Calibration and updating of the calibration time corresponding to their calibration intervals are performed for each of the other analysis items Na, K, Cl, GOT, CPK and CRTN, in the same manner as described above.

Assuming that the apparatus is operated for 24 hours, the result of an analysis of, for example, the analysis item GLU reveals that the amount of the reagent used is $1.8 \text{ ml} \times 12 = 21.6 \text{ ml}$, or ½ that of a conventional apparatus which performs calibration every hour. Simultaneously, in the apparatus of the present invention, the amount of standard serum is reduced as compared to the conventional apparatus. A stop time period for the reaction line can also be shortened as compared to the conventional apparatus which performs calibration of all analysis items every hour.

As well, in this apparatus, the operator can cause the display 3 to display the calibration menu 6 by operating the input device 1. For example, Nos. 1 to 5 in the calibration menu 6 are set to correspond to $CO_2$, GLU, GOT, CPK and CRTN, and Nos. 19 to 21 are set to correspond to Na, K and Cl.

After 1 hour and 6 minutes has elapsed from the first calibration time (0 hour), the calibration menu 6 is displayed on the display 3. In this case, the first calibration for all the items has been completed. When the calibration sample is sampled, the control device 5 supplies, to the display 3, a signal indicating that calibration for all the items is completed. As a result, a calibration end symbol "0" is displayed next to each analysis item on the display screen of the display 3. When 1 hour and 6 minutes has elapsed from the first calibration, since only the calibration interval of $CO_2$ has elapsed, the analysis item name $CO_2$ is flashed. When the calibration is not completed after the corresponding calibration interval, a symbol "." indicating non-calibration is displayed, as in the column for $CO_2$ of FIG. 3. When calibration is performed, the symbol "." is changed to "0".

In this manner, the operator can quickly recognize the analysis items after the calibration interval on a table, and can easily request the next calibration in accordance therewith.

The present invention is not limited to the above embodiment, and various changes and modifications may be made within the spirit and scope of the present invention.

In the embodiment, calibration is performed for 8 analysis items. However, the number of analysis items can be freely selected.

In the above embodiment, the calibration alarm data (FIG. 4), the calibration indication data (FIG. 5) and the calibration menu 6 are individually displayed on the display 3, but can be simultaneously displayed thereon.

What is claimed is:

1. In an automatic chemical analyzer having means for containing a sample to be analyzed, means for forming a reaction solution comprised of a mixture of the sample and a reagent corresponding to an analysis item, and means for analyzing the analysis item in the above mixture and wherein an output is provided in response to a quantitative analysis result obtained by comparing a measured reaction of said solution to a calibration curve corresponding to a respective analysis item, the improvement of:

means for storing the identity of a plurality of analysis items;

means for storing data indicating the time of a previous calibration of the calibration curve for each of the identified analysis items;

means for storing data corresponding to a predetermined time interval following the calibration of each calibration curve, said time interval corresponding to the time from a previous calibration that the calibration curve can be reliably substantially effective for analysis;

control means including counting means for checking periodically the time interval remaining for each previous calibration of the calibration curve for a respective analysis item; and means governed by said counting means for outputting data representative of the reliability of each checked calibration curve.

2. The improvement of claim 1, wherein the control means further includes means for outputting data corresponding to an information table indicating expiration of the predetermined time period for respective analysis items.

3. The improvement fo claim 1, further comprising alarm means governed by the control means for indicating expiration of the predetermined time interval.

4. The improvement of claim 2, further comprising display means for displaying said reliability and information table data.

5. A method of determining the reliability of each of a plurality of different calibration curves in an automatic chemical analyzer wherein measurement of a reaction solution comprised of a sample of the item to be analyzed and at least one reagent analysis item is compared to a respective calibration curve, said method comprising:

containing samples of the items to be analyzed;

storing data representative of the identify of a plurality of analysis items;

forming the reaction solution comprised of a mixture of said sample and a reagent corresponding to a respective analysis item;

quantitatively analyzing the analysis items in accordance with a corresponding calibration curve and producing output data in response to the analysis result;

storing first data for each of the plurality of analysis items indicative of the times of the previous calibration of a respective calibration curve;

storing second data for each of said plurality of analysis items corresponding to a predetermined time interval during which a respective calibration curve is substantially reliably effective following a calibration;

checking the remaining effective reliability time in accordance with the stored first and second data for each stored analysis item; and outputting data representative of the reliability of the calibration curve being checked.

6. A method according to claim 5 further including outputting data in the form of an information table indicating for respective stored analysis items the expirataion of the corresponding stored predetermined time interval.

7. A method according to claim 6 further including: displaying the reliability and information table data.

8. A method according to claim 6 further including: generating an alarm upon the expiration of a predetermined time interval for a respective identified item.

* * * * *